United States Patent
Miyamoto (10) Patent No.: US 11,406,494 B2
(45) Date of Patent: Aug. 9, 2022

(54) PROSTHETIC VALVE FORMING TEMPLATE AND PROSTHETIC VALVE

(71) Applicant: Shinka Miyamoto, Musashino (JP)

(72) Inventor: Shinka Miyamoto, Musashino (JP)

(73) Assignee: Shinka Miyamoto, Musashino (JP)

( * ) Notice: Subject to any disclaimer, the term of this patent is extended or adjusted under 35 U.S.C. 154(b) by 0 days.

(21) Appl. No.: 17/267,763

(22) PCT Filed: Jul. 29, 2020

(86) PCT No.: PCT/JP2020/028978
§ 371 (c)(1),
(2) Date: Feb. 10, 2021

(87) PCT Pub. No.: WO2021/020420
PCT Pub. Date: Feb. 4, 2021

(65) Prior Publication Data
US 2022/0142775 A1 May 12, 2022

(30) Foreign Application Priority Data

Jul. 29, 2019 (JP) .............................. JP2019-139081
Nov. 14, 2019 (JP) .............................. JP2019-206150

(51) Int. Cl.
*A61F 2/24* (2006.01)

(52) U.S. Cl.
CPC .......... *A61F 2/2415* (2013.01); *A61F 2/2418* (2013.01); *A61F 2240/005* (2013.01)

(58) Field of Classification Search
CPC ........ A61F 2/24; A61F 2/2415; A61F 2/2418; A61F 2240/005
(Continued)

(56) References Cited

U.S. PATENT DOCUMENTS 5,415,667 A 5/1995 Frater
5,554,184 A 9/1996 Machiraju
(Continued)

FOREIGN PATENT DOCUMENTS

EP 0583410 B1 7/2001
EP 0957829 B1 12/2005
(Continued)

OTHER PUBLICATIONS

Office Action issued in corresponding JP Application No. 2019-139081 dated Sep. 17, 2019 (2 pages).
(Continued)

*Primary Examiner* — Suzette J Gherbi
(74) *Attorney, Agent, or Firm* — Fitch, Even, Tabin & Flannery LLP (57) ABSTRACT

A prosthetic valve forming template having an annulus stitching part to be stitched to a mitral annulus, a papillary muscle stitching part to be stitched to papillary muscles, the prosthetic valve forming template including: one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines; and one second curved line extending upward in a parabolic manner from inner ends of the two second horizontal lines.

25 Claims, 6 Drawing Sheets (58) Field of Classification Search
USPC .................................................. 623/2.1–2.19
See application file for complete search history.

(56) References Cited

U.S. PATENT DOCUMENTS

| | | | |
|---|---|---|---|
| 6,214,055 | B1 | 4/2001 | Simionescu et al. |
| 6,358,277 | B1 | 3/2002 | Duran |
| 6,911,043 | B2* | 6/2005 | Myers .................... A61F 2/2415 |
| | | | 623/2.13 |
| 8,603,162 | B2* | 12/2013 | Umezu ................. A61F 2/2415 |
| | | | 623/2.12 |
| 10,779,939 | B2* | 9/2020 | Hariton ................. A61F 2/2418 |
| 2004/0117009 | A1 | 6/2004 | Cali et al. |
| 2004/0122513 | A1 | 6/2004 | Navia et al. |
| 2004/0138743 | A1* | 7/2004 | Myers .................... A61F 2/2415 |
| | | | 623/2.13 |
| 2020/0054448 | A1* | 2/2020 | Badhwar ............... A61F 2/2415 |
| 2021/0212818 | A1* | 7/2021 | Benton ............... B23K 26/0006 |
| 2021/0228347 | A1* | 7/2021 | Fish ....................... A61F 2/2418 |
| 2021/0275305 | A1* | 9/2021 | Pham ...................... A61F 2/243 |

FOREIGN PATENT DOCUMENTS

| | | |
|---|---|---|
| JP | H05-509013 A | 12/1993 |
| JP | 2009-077838 A | 4/2009 |
| JP | 2010-148633 A | 7/2010 |
| JP | 2010-527249 A | 8/2010 |
| JP | 3175944 U | 6/2012 |
| JP | 5106019 B2 | 12/2012 |
| JP | 5392539 B2 | 1/2014 |
| JP | 6411043 B2 | 10/2018 |
| WO | 2015/141798 A1 | 9/2015 |

OTHER PUBLICATIONS

Office Action issued in corresponding JP Application No. 2019-206150 dated Dec. 17, 2019 (2 pages).

International Search Report for PCT/JP2020/028978, dated Oct. 13, 2020, and English Translation submitted herewith (7 pages).

Supplementary European Search Report issued in corresponding EP Application No. 20829768.9 dated Mar. 14, 2022 (6 pages).

* cited by examiner

PROSTHETIC VALVE FORMING TEMPLATE AND PROSTHETIC VALVE

CROSS-REFERENCE TO RELATED APPLICATIONS

This application is a U.S. national phase application filed under 35 U.S.C. § 371 of International Application Number PCT/JP2020/028978, filed Jul. 29, 2020, designating the United States, which claims priority from Japanese Application Number 2019-206150, filed Nov. 14, 2019, and claims priority from Japanese Application Number 2019-139081, filed Jul. 29, 2019.

FIELD OF THE INVENTION

The present invention relates to a prosthetic valve forming template and a prosthetic valve.

BACKGROUND OF THE INVENTION

In association with aging of population, the number of cases of surgical operation for valvular disease in a field of cardiovascular surgery have been continued to rise every year.

The valvular disease is a disorder that impede normal functioning of heart valves, and includes "stenosis" in which a blood flow is constricted due to insufficient opening of the valve, and "closure insufficiency" in which closing of the valve is insufficient, which can result in backflow of blood. Typical examples of such diseases include aortic stenosis, aortic regurgitation, mitral stenosis, mitral regurgitation, tricuspid stenosis, and tricuspid insufficiency. Among these diseases, especially in recent years, the cases of aortic stenosis and mitral regurgitation rise significantly among aged people.

Examples of therapeutic methods for valvular disease include: an operative procedure of excising a dysfunctional valve due to diseases such as stenosis or closure insufficiency entirely, and then replacing with a prosthetic valve (hereinafter, referred to as "valve replacement procedure"); an operative procedure of excising an abnormal valve leaflet with autologous valve conserved and then re-stitching the excited site; and an operative procedure of regenerating the valve by excising an abnormal valve leaflet with autologous valve conserved and then stitching a valve leaflet formed of a biological membrane (hereinafter the above-described operative procedure of re-stitching and the above-described operative procedure of regeneration are collectively referred to also as "valvuloplasty"). In addition, therapies using catheters (such as transcatheter aortic valve replacement procedures) are also employed positively in recent years.

Among the therapeutic methods described above, the valvuloplasty is considered to provide better prognosis compared with the valve replacement procedure because functional and morphological continuities of the valve are likely to be maintained. Furthermore, the valvuloplasty has a merit that it has less risk for complicating diseases such as thrombosis because autologous valves can be used.

As regards the valvuloplasty, a technology relating to a template for obtaining valve leaflet material is disclosed (Patent Literatures 1 and 2).

In contrast, when the valve or the cardiac muscle is significantly damaged, the valve replacement procedure is suitable.

For the moment, the valve replacement procedure is a standard of care for each of diseases such as stenosis and/or closure insufficiency of atrioventricular valves (mitral valve and/or tricuspid valve).

The valve replacement procedure for atrioventricular valves is an open chest surgery in which an involved atrioventricular valve is totally excised and replaced with a prosthetic valve. The prosthetic valve is classified into two types including mechanical valves made of a prosthetic material such as carbon, and biological valves made of materials originating from biological subjects such as bovine pericardiums or pig pericardiums.

In past days, the mechanical valves were used frequently in the valve replacement procedure for atrioventricular valves. However, in recent years, frequency in use of the biological valves rises significantly in association with aging of patients.

Figure 8:
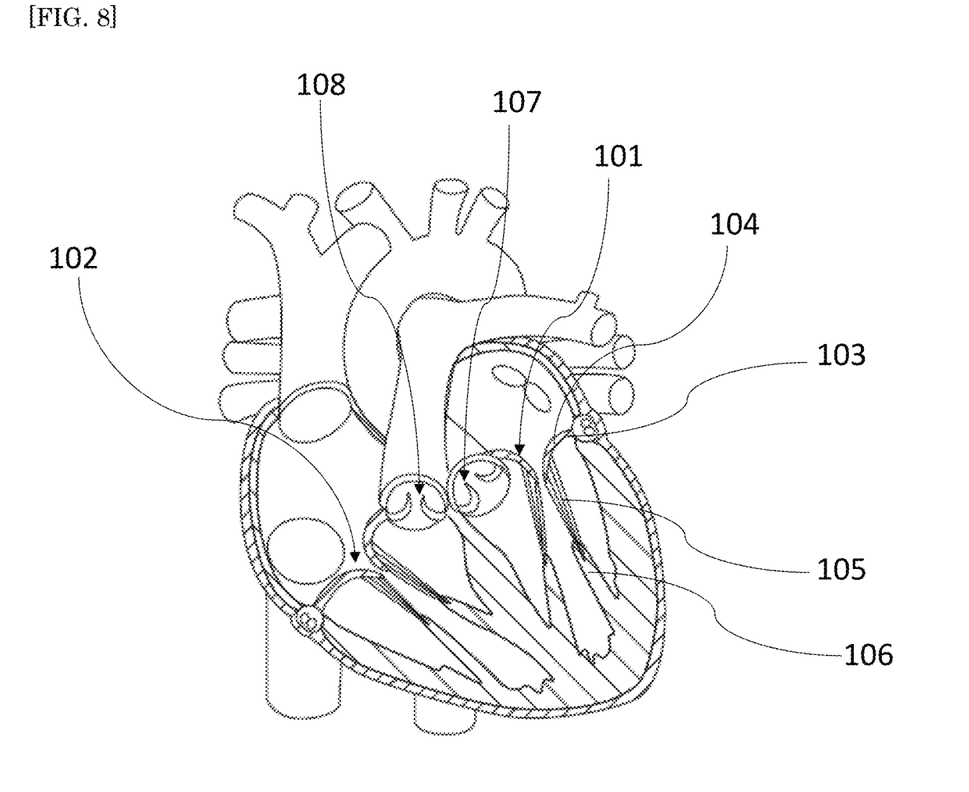
FIG. 8 is a schematic drawing of a heart.

As illustrated in FIG. 8, the atrioventricular valves (a mitral valve 101 and/or a tricuspid valve 102) are each made up of a complex including, continuing from an annulus part 103, a valve leaflet 104, tendinous cords 105 and papillary muscles 106. Employed in the valve replacement procedure of the atrioventricular valves in the related art is an operative procedure including excising the valve leaflet 104 and the tendinous cords 105, inverting a biological valve having a structure similar to a semilunar valve (an aortic valve 107 and/or a pulmonary valve 108) upside down, and stitching the same only to the annulus part. Such biological valves in the related art have neither a part corresponding to the tendinous cords nor a connection with the papillary muscles, and thus are quite different morphologically, anatomically, and physiologically from normal atrioventricular valves. Therefore, when replacement of the mitral valve is performed by using the biological valves in the related art, cardiac dysfunction after surgery is a challenge due to a loss of connection from the annulus to the papillary muscles.

A prosthetic mitral valve provided with a ring and a prosthetic cusp having a specific structure continuing along a peripheral edge of the ring is disclosed as a prosthetic mitral valve which can achieve a valve behavior similar to the actual mitral valve (Patent Literature 3).

However, the prosthetic mitral valve disclosed in Patent Literature 3 has a risk of infection and thromboembolism in association with a use of the ring, which is an artifact for correcting or reinforcing the annulus.

Furthermore, the prosthetic mitral valve disclosed in Patent Literature 3 has a problem in that the structure including a plurality of valve leaflet members and rings is complicated.

CITATION LIST

Patent Literatures

PTL 1: Japanese Patent No. 6411043
PTL 2: Japanese Patent No. 5106019
PTL 3: Japanese Patent No. 5392539

SUMMARY OF INVENTION

In view of such circumstances, it is a subject that the present invention is to solve to provide a technology relating to a prosthetic valve having a simple structure, being free from a loss of connection from an annulus part to papillary muscles even after a surgery of valve replacement procedure, and being capable of avoiding a risk of infection and thromboembolism in association with the use of a ring, which is an artifact.

As used herein the term "technology relating to the prosthetic valve" is intended to mean a prosthetic valve forming template used for forming the prosthetic valve, and a prosthetic valve formed by using the prosthetic valve forming template.

As a result of earnest investigation, the present inventors have found that the above-described problems can be solved by a prosthetic valve forming template having a specific shape. The present invention is achieved based on the following knowledge.

The present invention provides the following items from [1] to [8].

(Prosthetic Valve Forming Template: for Mitral Valve)

[1] A prosthetic valve forming template for forming a prosthetic valve having an annulus stitching part to be stitched to a mitral annulus, an anterior papillary muscle stitching part to be stitched to an anterior papillary muscle, and a posterior papillary muscle stitching part to be stitched to a posterior papillary muscle, the prosthetic valve forming template including:

one base line;

two drooping lines suspending from both ends of the base line;

two sidelines extending respectively downward and inward in a semi-parabolic manner from lower ends of the two drooping lines;

two first horizontal lines extending respectively inward and horizontally from lower ends of the two sidelines;

two first curved lines extending respectively upward in a parabolic manner from inner ends of the two first horizontal lines;

two second horizontal lines extending respectively inward and horizontally from inner ends of the two first curved lines; and one second curved line extending upward in a parabolic manner from inner ends of the two second horizontal lines.

(Prosthetic Valve Forming Template: for Tricuspid Valve)

[2] A prosthetic valve forming template for forming a prosthetic valve having an annulus stitching part to be stitched to a tricuspid annulus, a medial papillary muscle stitching part to be stitched to a medial papillary muscle, and a posterior papillary muscle stitching part to be stitched to a posterior papillary muscle, the prosthetic valve forming template including:

one base line;

two drooping lines suspending from both ends of the base line;

two sidelines extending respectively downward and inward in a semi-parabolic manner from lower ends of the two drooping lines;

two first horizontal lines extending respectively inward and horizontally from lower ends of the two sidelines;

two first curved lines extending respectively upward in a parabolic manner from inner ends of the two first horizontal lines; and one second horizontal line connecting inner ends of the two first curved lines.

(Prosthetic Valve Forming Template: for Aorta)

[3] A prosthetic valve forming template for forming a prosthetic valve having an annulus stitching part to be stitched or crimped to an aortic valve annulus, and two aortic wall stitching parts to be stitched to an aortic wall, the prosthetic valve forming template including:

one base line;

two drooping lines suspending from both ends of the base line;

two sidelines extending respectively downward and inward in a semi-parabolic manner from lower ends of the two drooping lines;

two first horizontal lines extending respectively inward and horizontally from lower ends of the two sidelines;

two first curved lines extending respectively upward in a parabolic manner from inner ends of the two first horizontal lines;

two second horizontal lines extending respectively inward and horizontally from inner ends of the two first curved lines; and one second curved line extending upward in a parabolic manner from inner ends of the two second horizontal lines.

(Prosthetic Valve Forming Template: for Pulmonary Artery)

[4] A prosthetic valve forming template for forming a prosthetic valve having an annulus stitching part to be stitched or crimped to a pulmonary valve annulus, and two pulmonary artery wall stitching parts to be stitched to a pulmonary artery wall, the prosthetic valve forming template including:

one base line;

two drooping lines suspending from both ends of the base line; two sidelines extending respectively downward and inward in a semi-parabolic manner from lower ends of the two drooping lines;

two first horizontal lines extending respectively inward and horizontally from lower ends of the two sidelines;

two first curved lines extending respectively upward in a parabolic manner from inner ends of the two first horizontal lines;

two second horizontal lines extending respectively inward and horizontally from inner ends of the two first curved lines; and one second curved line extending upward in a parabolic manner from inner ends of the two second horizontal lines.

(Prosthetic Valve: for Mitral Valve)

[5] A prosthetic valve having an annulus stitching part to be stitched to a mitral annulus, an anterior papillary muscle stitching part to be stitched to an anterior papillary muscle, and a posterior papillary muscle stitching part to be stitched to a posterior papillary muscle, the prosthetic valve being made by using a membrane member including: one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines; and one second curved line extending upward in a parabolic manner from inner ends of the two second horizontal lines, the annulus stitching part being formed by folding back the base line vertically downward with respect to a plane including the anterior papillary muscle stitching part and the posterior papillary muscle stitching part, and then aligning the two drooping lines with each other and stitching together, the anterior papillary muscle stitching part being formed by overlapping the two second horizontal lines, the posterior papillary muscle stitching part being formed by overlapping the two first horizontal lines, and the prosthetic valve including:

a barrel cylindrical part opening vertically upward with respect to a plane including the anterior papillary muscle stitching part and the posterior papillary muscle stitching part, and including the annulus stitching part, and a bifurcated part continuing from the barrel cylindrical part, the bifurcated part including the anterior papillary muscle stitching part at a distal end and the posterior papillary muscle stitching part at an opposite distal end.

[6] (Prosthetic Valve: for Tricuspid valve)

A prosthetic valve having an annulus stitching part to be stitched to a tricuspid annulus, a medial papillary muscle stitching part to be stitched to a medial papillary muscle, and a posterior papillary muscle stitching part to be stitched to a posterior papillary muscle, the prosthetic valve being made by using a membrane member including: one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; and one second horizontal line connecting inner ends of the two first curved lines, the annulus stitching part being formed by folding back the base line vertically downward with respect to a plane including the medial papillary muscle stitching part and the posterior papillary muscle stitching part, and then aligning the two drooping lines with each other and stitching together, the medial papillary muscle stitching part being formed by folding the one second horizontal line at a center point and overlapping one side on top of another, the posterior papillary muscle stitching part being formed by overlapping the two first horizontal lines, and the prosthetic valve including:
a barrel cylindrical part opening vertically upward with respect to a plane including the medial papillary muscle stitching part and the posterior papillary muscle stitching part, and including the annulus stitching part, and
a bifurcated part continuing from the barrel cylindrical part, the bifurcated part including the medial papillary muscle stitching part at a distal end and the posterior papillary muscle stitching part at an opposite distal end.

(Prosthetic Valve: for Aortic Valve)

[7] A prosthetic valve having an annulus stitching part to be stitched or crimped to an aortic valve annulus, and two aortic wall stitching parts to be stitched to an aortic wall, the prosthetic valve being made by using a membrane member including:

one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines; and one second curved line extending upward in a parabolic manner from inner ends of the two second horizontal lines, the annulus stitching part being formed by folding back the base line vertically downward with respect to a plane including the two aortic wall stitching parts, and then aligning the two drooping lines with each other and stitching together, one of the aortic wall stitching parts being formed by overlapping the two second horizontal lines, one of the aortic wall stitching parts being formed by overlapping the two first horizontal lines, the prosthetic valve including:
a barrel cylindrical part opening vertically upward with respect to a plane including the two aortic wall stitching parts, and including the annulus stitching part, and
a bifurcated part continuing from the barrel cylindrical part, the bifurcated part including the two aortic wall stitching parts at distal ends thereof.

(Prosthetic Valve: for Pulmonary Valve)

[8] A prosthetic valve having an annulus stitching part to be stitched or crimped to a pulmonary valve annulus, and two pulmonary artery wall stitching parts to be stitched to a pulmonary artery wall, the prosthetic valve being made by using a membrane member including: one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines; and one second curved line extending upward in a parabolic manner from inner ends of the two second horizontal lines, the annulus stitching part being formed by folding back the base line vertically downward with respect to a plane including the two pulmonary artery wall stitching parts, and then aligning the two drooping lines with each other and stitching together, one of the pulmonary artery wall stitching parts being formed by overlapping the two second horizontal lines, one of the pulmonary artery wall stitching parts being formed by overlapping the two first horizontal lines, the prosthetic valve including:
a barrel cylindrical part opening vertically upward with respect to a plane including the two pulmonary artery wall stitching parts, and including the annulus stitching part, and
a bifurcated part continuing from the barrel cylindrical part, the bifurcated part including the two pulmonary artery wall stitching parts at distal ends thereof.

A prosthetic valve forming template according to an embodiment of the present invention is a prosthetic valve forming template for forming a prosthetic valve having an annulus stitching part to be stitched to a mitral annulus, an anterior papillary muscle stitching part to be stitched to an anterior papillary muscle, and a posterior papillary muscle stitching part to be stitched to a posterior papillary muscle, the prosthetic valve forming template having a simple structure including: one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines;

and one second curved line extending upward in a parabolic manner from inner ends of the two second horizontal lines. The shape of a portion surrounded by lines including these lines corresponds to a form obtained by developing normal mitral valve, tendinous cords, and papillary muscles.

A membrane having substantially the same shape as the prosthetic valve forming template is obtained by preparing the above-described prosthetic valve forming template, placing the prosthetic valve forming template on a membrane for forming the prosthetic valve, and cutting off the membrane along an outer periphery thereof. With the membrane after having cut off, a prosthetic valve having a simple structure can be obtained by folding a part corresponding to the base line of the prosthetic valve forming template downward, then aligning parts corresponding to the two drooping lines with each other and stitching together to form an annulus stitching part, overlapping parts corresponding to the two second horizontal lines with each other to form the anterior papillary muscle stitching part, and overlapping parts corresponding to the two first horizontal lines with each other to form the posterior papillary muscle stitching part.

At the time of procedure, valve replacement is performed by excising involved atrioventricular valve and tendinous cord, stitching the anterior papillary muscle stitching part of the prosthetic valve to an anterior papillary muscle, stitching the posterior papillary muscle stitching part to the posterior papillary muscle, and stitching the annulus stitching part to a mitral annulus.

A part situated between lines corresponding to the first curved lines and the second curved line of the prosthetic valve forming template has a bifurcated shape, and has a function corresponding to a tendinous cord. Therefore, according to the prosthetic valve having the structure described above, the connection from the annulus part to the papillary muscles is maintained like a normal mitral valve.

As described above, through placing the prosthetic valve forming template on a membrane for forming the prosthetic valve, cutting off the membrane along the outer periphery thereof to obtain a membrane having substantially the same shape as the prosthetic valve forming template, folding back the part of the membrane member corresponding to the base line downward, and aligning the parts corresponding to the two drooping lines with each other and stitching together to form an annulus stitching part, usage of the ring, which is an artifact for correcting or reinforcing the annulus, is no longer necessary, so that the risk of infection and thromboembolism in association with the usage of the artifact can be avoided.

DESCRIPTION OF EMBODIMENTS

The present invention will be described in detail below. However, the present invention is not limited to embodiments described below.

The present invention relates to a prosthetic valve forming template for forming a prosthetic valve used for performing valve replacement procedure for mammals including humans, dogs, cats, sheep, cows, pigs, goats, rabbits that have developed valvular disease, and a prosthetic valve formed by using the prosthetic valve forming template.

Embodiment 1: Mitral Valve

In the present embodiment, a prosthetic valve forming template and a prosthetic valve used in valve replacement procedure of a human mitral valve will be described.

Figure 1:
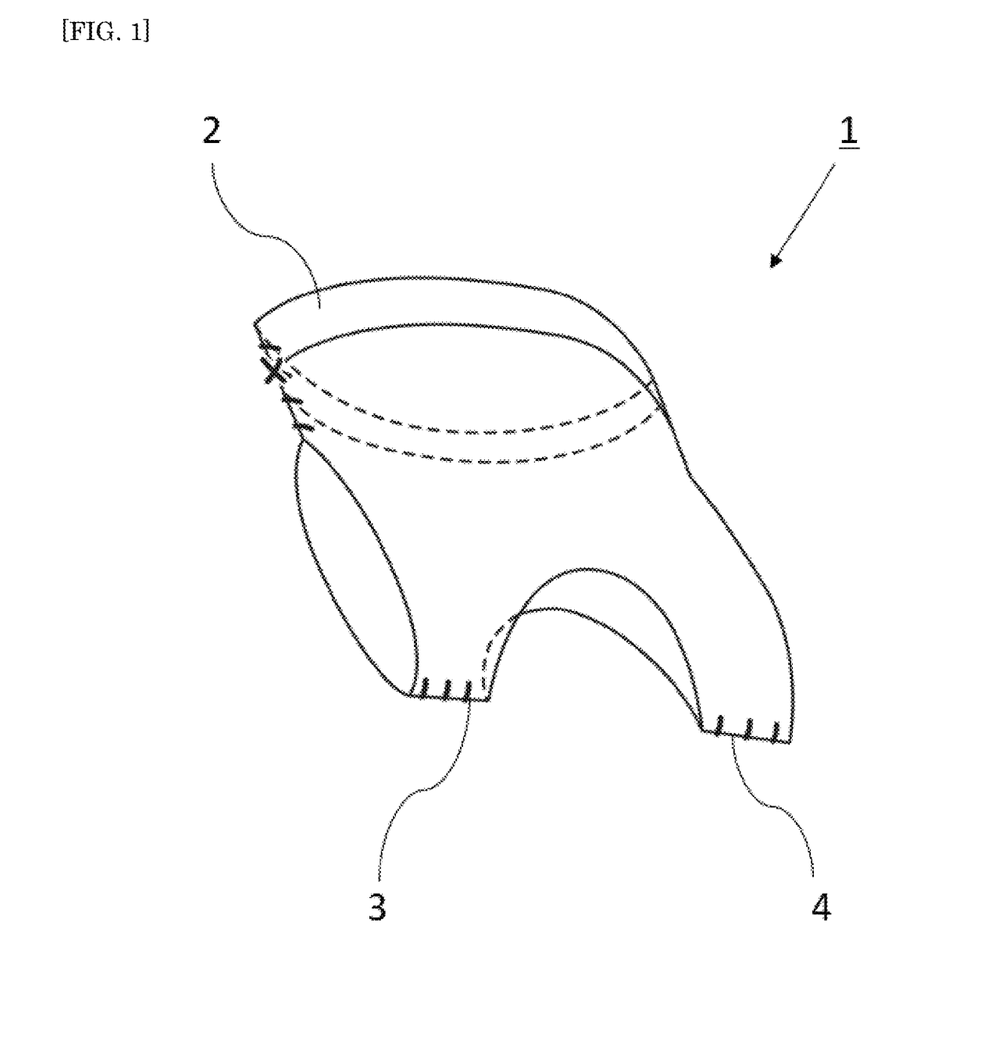
FIG. 1 is a general perspective view of a prosthetic valve according to an embodiment of the present invention.

The prosthetic valve forming template according to the present embodiment can be used for an application for forming a prosthetic valve 1 illustrated in FIG. 1, specifically, the prosthetic valve 1 having an annulus stitching part 2 to be stitched to a mitral annulus, and an anterior papillary muscle stitching part 3 to be stitched to an anterior papillary muscle, and a posterior papillary muscle stitching part 4 to be stitched to a posterior papillary muscle.

(Prosthetic Valve Forming Template used in Valve Replacement Procedure of Mitral Valve)

Figure 2:
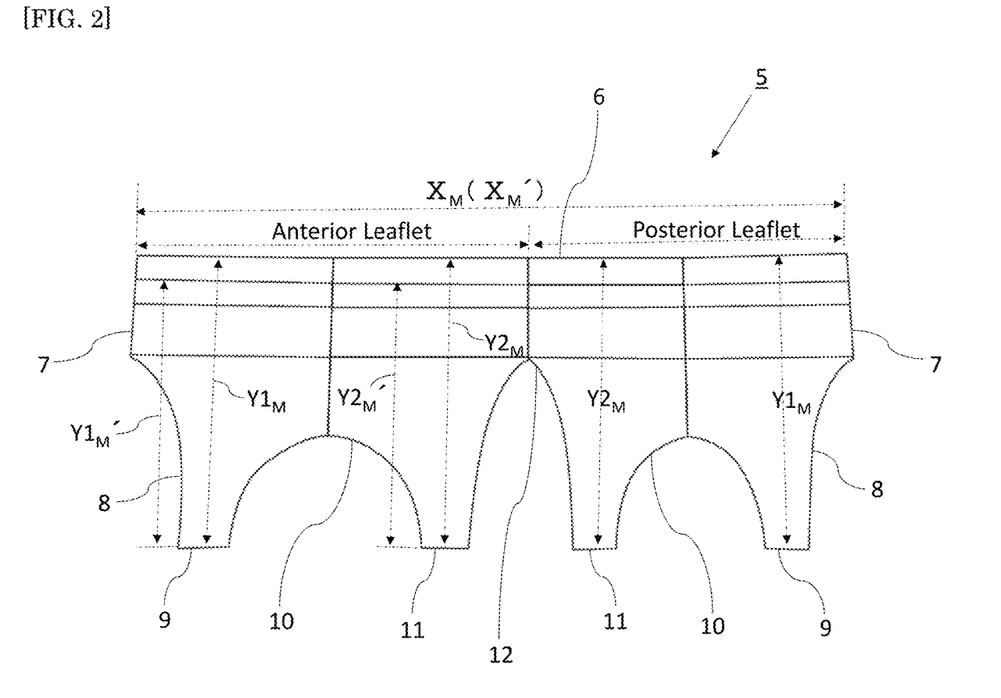
FIG. 2 is a front view of a prosthetic valve forming template according to the embodiment of the present invention.

A prosthetic valve forming template 5 of the present embodiment includes, as illustrated in FIG. 2, one base line 6; two drooping lines 7 suspending from both ends of the base line; two sidelines 8 extending respectively downward and inward in a semi-parabolic manner from lower ends of the two drooping lines 7; two first horizontal lines 9 extending respectively inward and horizontally from lower ends of the two sidelines 8; two first curved lines 10 extending respectively upward in a parabolic manner from inner ends of the two first horizontal lines 9; two second horizontal lines 11 extending respectively inward and horizontally from inner ends of the two first curved lines 10; and one second curved line 12 extending upward in a parabolic manner from inner ends of the two second horizontal lines 11.

The shape of a portion surrounded by lines including these lines corresponds to a shape obtained by developing normal mitral valve, tendinous cords, and papillary muscles.

Figure 3:
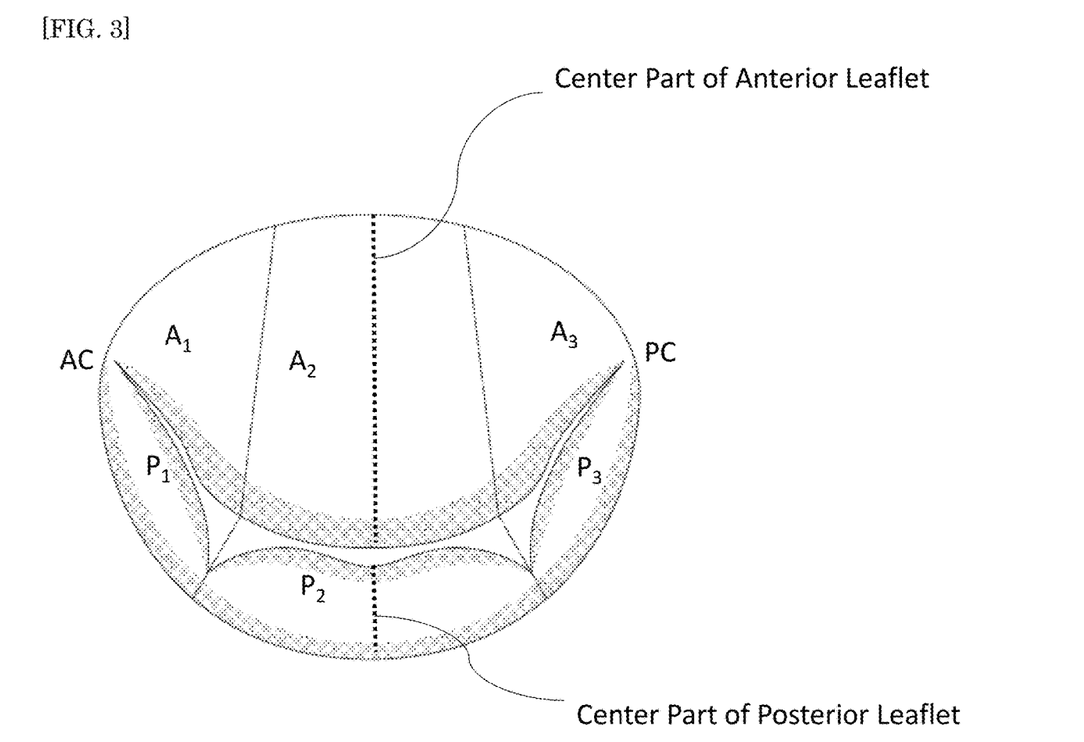
FIG. 3 is a top view of a mitral valve.

The normal mitral valve includes, as illustrated in FIG. 3, an anterior leaflet ($A_1$ to $A_3$) and a posterior leaflet ($P_1$ to $P_3$). As used herein the term "the shape obtained by developing normal mitral valve, tendinous cords, and papillary muscles" is intended to mean a shape connecting a shape surrounded by a broken line in FIG. 4(a) and a shape surrounded by a broken line in FIG. 4(b).

Figure 4:
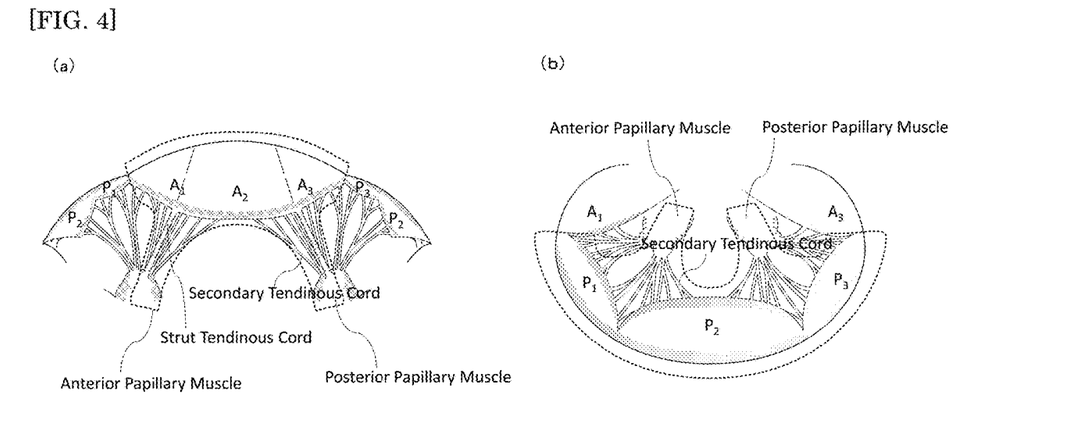
FIG. 4(a) is a top view of the mitral valve in FIG. 3 in a state of being cut and developed at a center of a posterior leaflet.
FIG. 4(b) is a top view of the mitral valve in FIG. 3 in a state of being cut and developed at a center of an anterior leaflet.

As illustrated in FIG. 4(a), a number of secondary tendinous cords are connected mainly to a center part ($A_2$) of the anterior leaflet, and likewise, as illustrated in FIG. 4(b), a number of secondary tendinous cords are connected mainly to a center part ($P_2$) of the posterior leaflet. As used herein, the term "secondary tendinous cords" is intended to mean tendinous cords starting from the papillary muscles and attached to the mitral valve.

A part of the prosthetic valve forming template 5 surrounded by the sidelines 8, the first horizontal lines 9, the first curved lines 10, the second horizontal lines 11, and the second curved line 12 (a part having a "bifurcated shape" of the prosthetic valve forming template) corresponds to a form including the secondary tendinous cords attached to the center part ($A_2$) of the anterior leaflet and the center part ($P_2$) of the posterior leaflet.

However, while the secondary tendinous cords of the normal mitral valve are such that the secondary tendinous cords of the anterior leaflet are longer than the secondary tendinous cords of the posterior leaflet, both of ($Y1_M$) and ($Y2_M$) in the prosthetic valve forming template 5 of the present embodiment are designed with reference to a thickest strut tendinous cords among the secondary tendinous cords attached to the center part ($A_2$) of the anterior leaflet. Accordingly, a swelled shape of the posterior leaflet is achieved after the valve replacement.

A length ($X_M$) of the base line 6 is preferably a length ($X_M$) corresponding to a perimeter of the mitral annulus of a patient subjected to the valve replacement (hereinafter, referred to as "patient").

As used herein, the term "length corresponding to" is intended to mean "substantially the same length as". Errors caused by manual operation such as measurement or cutting are included in the range of "substantially the same".

A length of a direct distance ($Y1_M$) from the base line 6 to the first horizontal lines 9 of the prosthetic valve forming template 5 is preferably from 107.5% to 109.5%, and more preferably, from 108.0% to 109.0, of a length ($Y1_M'$) corresponding to a direct length between an anterior leaflet annulus of the mitral valve and a posterior papillary muscle of the mitral valve of the patient.

A length of a direct distance ($Y2_M$) from the base line 6 to the second horizontal lines 11 of the prosthetic valve forming template 5 is preferably from 107.5% to 109.5%, and more preferably, from 108.0% to 109.0, of a length ($Y2_M'$) corresponding to a direct length between the anterior leaflet annulus of the mitral valve and an anterior papillary muscle of the mitral valve of the patient.

As used herein the term "anterior leaflet annulus" is intended to mean the annulus of a mitral valve, including two valve leaflets referred to as "anterior leaflet" and "posterior leaflet", located on the anterior leaflet side, and the term "posterior leaflet annulus" means the annulus of a mitral valve located on the posterior leaflet side.

The $X_M'$, $Y1_M'$, and $Y2_M'$ can be measured at the time of performing the valve replacement procedure. A method of measurement can be achieved, for example, by, but not limited to, a method of starting extracorporeal circulation using a prosthetic heart-lung machine with the heart exposed, stopping the heart beat, excising an involved mitral valve by excising parts of the annulus part and the papillary muscles, and actually measuring the excised mitral valve. Examples of the method of actual measurement include a method of measurement using a sizer or a method of measuring a thread placed in conformity with a part to be measured and cut.

The $X_M'$, $Y1_M'$, and $Y2_M'$ can be measured before performing valve replacement procedure by transthoracic echocardiography and/or transesophageal echocardiography or MRI examination in advance.

(Prosthetic Valve used in Valve Replacement Procedure of Mitral Valve)

Subsequently, a prosthetic valve obtained by using the above-described prosthetic valve forming template 5 will be described.

The prosthetic valve of the present embodiment includes, as illustrated in FIG. 1, the annulus stitching part 2 to be stitched to the mitral annulus, the anterior papillary muscle stitching part 3 to be stitched to the anterior papillary muscle, the posterior papillary muscle stitching part 4 to be stitched to the posterior papillary muscle of the mitral valve.

The prosthetic valve of the present embodiment can be obtained in the following manner.

First, the prosthetic valve forming template 5 illustrated in FIG. 2 is placed on a pericardium, which is a membrane member, and the pericardium is cut off along an outer periphery thereof, so that a pericardium having substantially the same shape as the prosthetic valve forming template 5 is obtained.

Subsequently, a part of the pericardium having substantially the same shape as the prosthetic valve forming template 5 corresponding to the base line of the prosthetic valve forming template 5 is folded back downward, and parts corresponding to the two drooping lines are aligned with each other and are stitched together to form the annulus stitching part 2. Further, parts of the pericardium corresponding to the two second horizontal lines of the prosthetic valve forming template 5 are overlapped to form the anterior papillary muscle stitching part 3, and parts of the prosthetic valve forming template 5 corresponding to the two first horizontal lines are overlapped to form the posterior papillary muscle stitching part 4.

The vertical width of the annulus stitching part 2 (that is, a distance between the line corresponding to the base line after having folded back and the upper end of the annulus stitching part 2) is preferably a length from 7.5% to 9.5% of the $Y1_M$, and more preferably, a length from 8.0% to 9.0%. Accordingly, while maintaining the function equivalent to the function of the "ring" of the prosthetic valve in the related art, the risk of infection and thromboembolism in associated with the usage of the ring, which is an artifact can be avoided.

The prosthetic valve 1 having the structure as described above is implanted in the heart by stitching the annulus stitching part 2 to the mitral annulus of the patient, stitching the anterior papillary muscle stitching part 3 to the anterior papillary muscle of the patient, and stitching the posterior papillary muscle stitching part 4 to the posterior papillary muscle.

(Effects to be Found after Valve Replacement)

Since the part surrounded by lines corresponding to the sidelines 8, the first horizontal lines 9, the first curved lines 10, the second horizontal lines 11, and the second curved line 12 has a bifurcated shape and has a function corresponding to the tendinous cords 105, the connection from the annulus part to the papillary muscles is maintained in the same manner as the normal mitral valve, and thus the maintenance of the cardiac function after the replacement is expected according to the prosthetic valve 1 having the structure as described above.

According to the prosthetic valve 1 having the structure as described above and having the annulus stitching part 2, usage of the ring, which is an artifact for correcting or reinforcing the annulus in the related art, is no longer necessary, and thus the risk of infection and thromboembolism in association with the usage of the artifact can be avoided. Internal use of antithrombogenic agents or anticoagulant agent such as warfarin is not necessary as well.

With the prosthetic valve 1 prepared by using the prosthetic valve forming template 5 having a length ($X_M$) of the base line 6 corresponding to a length ($X_M'$) corresponding to the perimeter of the mitral annulus of the patient although the size of the mitral valve varies among individuals, valve replacement can be conducted by using the prosthetic valve having an optimum size even, for example, for narrow annulus (having a diameter of 15 mm or smaller) of new born babies, who could not receive the valve replacement procedure in the related art.

In addition, while the prosthetic valve in the related art, being provided outside the ring with a cloth (cuff) for stitching to the heart, can cause narrowing of a valve orifice area by an amount corresponding to the area of the cuff, the prosthetic valve of the present invention needs neither the ring nor the cuff, so that an effective valve orifice area suitable for the original heart can be obtained, and movement of the annulus part synchronous with systolic phase and diastolic phase can be maintained.

Furthermore, when the prosthetic valve of the present invention is used, a sufficient length of a joint surface is maintained, and thus backflow of the valve can be inhibited for a long term.

With the prosthetic valve prepared by using the prosthetic valve forming template 5 having the direct distance ($Y1_M$) from the base line 6 to the first horizontal lines 9 and the direct distance ($Y2_M$) from the base line 6 to the second horizontal lines 11 of the prosthetic valve forming template 5 set respectively to the lengths described above, the distance ($Y1_M'$) from the papillary muscles to the anterior leaflet annulus can be secured to be longer than the distance ($Y_M'$) from the papillary muscles to the posterior leaflet annulus in the same manner as the normal valve. Accordingly, when the valve is closed, the posterior leaflet can be moved in the same manner as the normal valve.

Furthermore, according to the prosthetic valve prepared by using the prosthetic valve forming template 5 having the $Y1_M$ and $Y2_M$ set respectively to the lengths described above, systolic anterior movement (SAM) of the mitral valve can be avoided.

The pericardium is preferably an autologous pericardium. Through usage of the autologous pericardium, occurrence of infection and hemolytic anemia can be avoided, and favorable tissue compatibility and longer sustention of tenderness are achieved.

While the autologous pericardium is preferable as the pericardium as described above, pericardiums of other species such as cow, horse, and pig, or a membrane made of a prosthetic material can also be used.

Embodiment 2: Tricuspid Valve

In the present embodiment, a prosthetic valve forming template and a prosthetic valve used in valve replacement procedure of a human tricuspid valve will be described. Description about the structure common to Embodiment 1 will be omitted.

Figure 5:
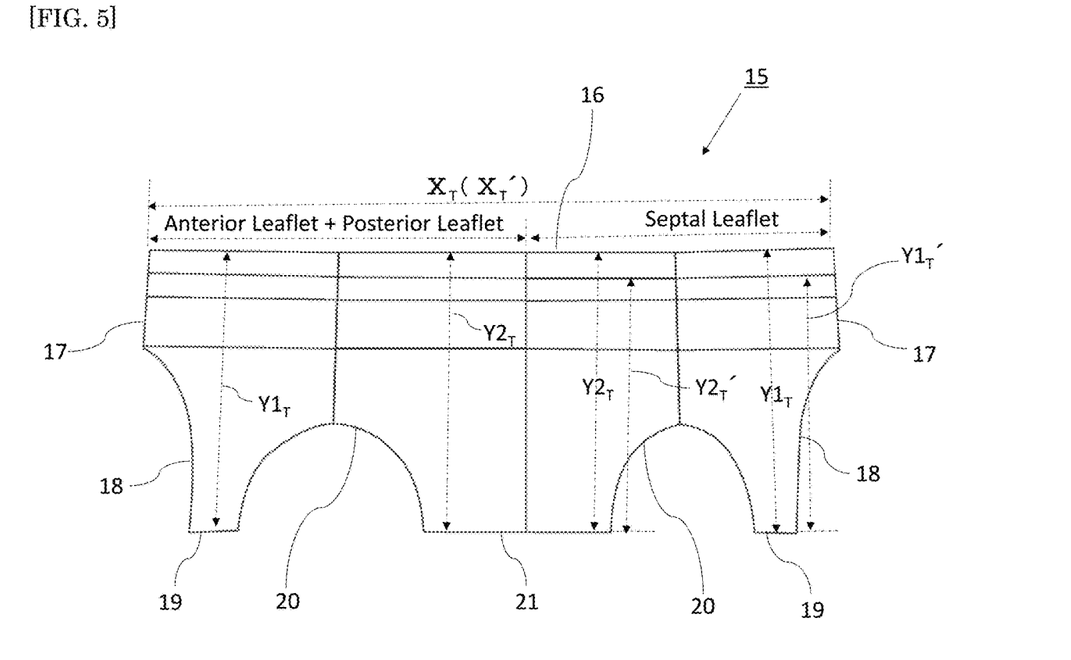
FIG. 5 is a front view of a prosthetic valve forming template according to another embodiment of the present invention.

A prosthetic valve forming template 15 of the present embodiment is the same as in Embodiment 1 in including, as illustrated in FIG. 5, one base line 16; two drooping lines 17 suspending from both ends of the base line 16; two sidelines 18 extending respectively downward and inward in a semi-parabolic manner from lower ends of the two drooping lines 17; two first horizontal lines 19 extending respectively inward and horizontally from lower ends of the two sidelines 18; and two first curved lines 20 extending respectively upward in a parabolic manner from inner ends of the two first horizontal lines 19. In contrast, Embodiment 2 is different in that lines corresponding to the two second horizontal lines 11 and the one second curved line 12 extending upward in a parabolic manner from the inner ends of the two second horizontal lines 11 in Embodiment 1 do not exist, but has one second horizontal line 21 connecting inner ends of the first curved lines 20.

Common to Embodiment 1, the prosthetic valve forming template 15 is placed on the pericardium, the pericardium is cut along an outer periphery thereof to obtain a pericardium having substantially the same shape as the prosthetic valve forming template 15 to form the annulus stitching part. Subsequently, parts corresponding to the two first horizontal lines 19 are overlapped to form a posterior papillary muscle stitching part, and a part corresponding to the one second horizontal line 21 is folded at a center point and overlapping one side on top of another to form the medial papillary muscle stitching part. The prosthetic valve having the structure as described above is implanted in the heart by stitching the annulus stitching part to the tricuspid annulus, stitching the anterior papillary muscle stitching part to a medial papillary muscle, and stitching the posterior papillary muscle stitching part to a posterior papillary muscle.

Figure 6:
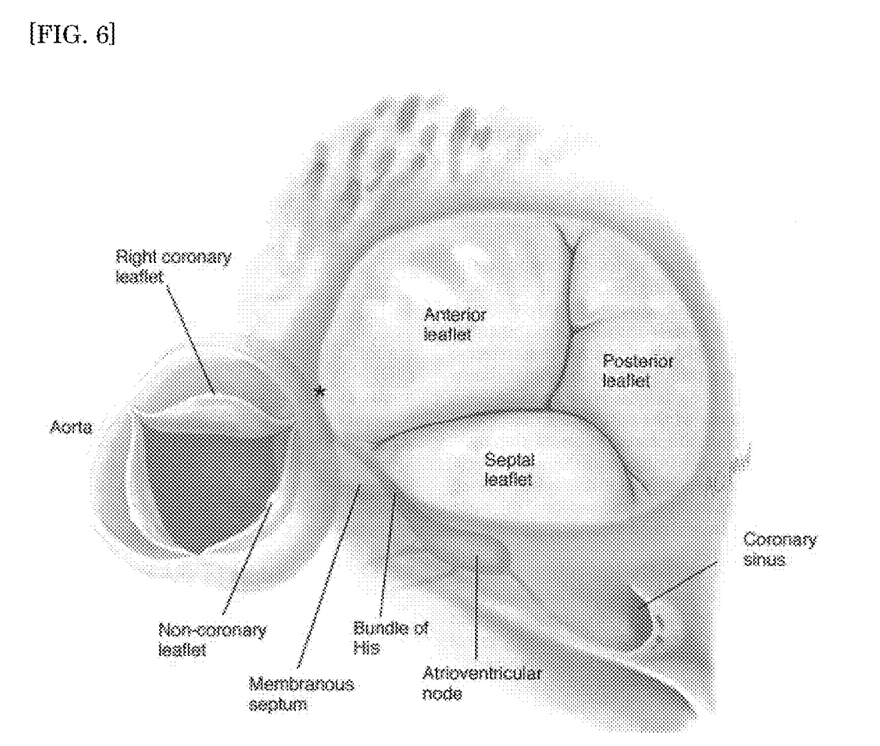
FIG. 6 is a top view of a tricuspid valve.
Figure 7:
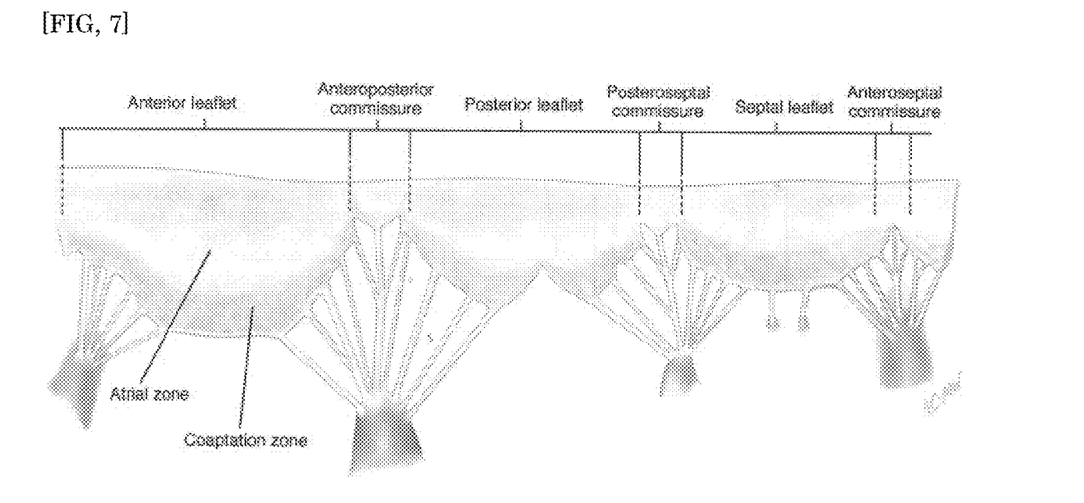
FIG. 7 is a developed view of the tricuspid valve.

The normal tricuspid valve includes an anterior leaflet, a posterior leaflet and a septal leaflet as illustrated in FIG. 6 and FIG. 7.

In general, in the valvuloplasty, while the valve is prepared by imitating the shape of the developed normal valve for the purpose of obtaining the form and function as close to the normal valve as possible, the prosthetic valve forming template 15 of the present embodiment has a structure achieved by simplifying the developed drawing in FIG. 7 as much as possible within a range that secure necessary and sufficient functions as the valve. Specifically, the prosthetic valve forming template 15 of the present embodiment has a shape similar to the template 5, which is the template for the mitral valve, except that the second curved line 12 is eliminated from the template 5, which is the template for the mitral valve.

Through the formation of the prosthetic valve of the tricuspid valve by using the prosthetic valve forming template 15 of the present embodiment, the prosthetic valve can be prepared in the simplest manner compared with that in the related art while maintaining the necessary and sufficient functions as the valve.

A prosthetic valve prepared by using the prosthetic valve forming template 15 of the present embodiment includes: one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; and one second horizontal line connecting inner ends of the two first curved lines, the prosthetic valve having an annulus stitching part to be stitched to a tricuspid annulus, a medial papillary muscle stitching part to be stitched to a medial papillary muscle, and a posterior papillary muscle stitching part to be stitched to a posterior papillary muscle, the annulus stitching part being formed by folding back the base line vertically downward with respect to a plane including the medial papillary muscle stitching part and the posterior papillary muscle stitching part, and then aligning the two drooping lines with each other and stitching together, the medial papillary muscle stitching part being formed by folding the one second horizontal line at a center point and overlapping one side on top of another, the posterior papillary muscle stitching part being formed by overlapping the two first horizontal lines, and the prosthetic valve including: a barrel cylindrical part opening vertically upward with respect to a plane including the medial papillary muscle stitching part and the posterior papillary muscle stitching part, and including the annulus stitching part, and a bifurcated part continuing from the barrel cylindrical part, the bifurcated part including the medial papillary muscle stitching part at a distal end and the posterior papillary muscle stitching part at an opposite distal end.

A length ($X_T$) of the base line 16 is preferably a length ($X'_T$) corresponding to a perimeter of the tricuspid annulus of a patient subjected to the valve replacement (hereinafter, referred to as "patient").

A length of a direct distance ($Y1_T$) from the base line 16 to the first horizontal lines 19 of the prosthetic valve forming template 15 is preferably from 109.5% to 112.5%, and more preferably, from 110.5% to 111.5, of a length ($Y1_T'$) corresponding to a direct length between a septal leaflet annulus and the posterior papillary muscle of the tricuspid valve of the patient.

A length of a direct distance ($Y2_T$) from the base line 16 to the second horizontal lines 21 of the prosthetic valve forming template 15 is preferably from 109.5% to 112.5%, and more preferably, from 110.5% to 111.5, of a length ($Y2_T'$) corresponding to a direct length between a septal leaflet annulus and the medial papillary muscle of the tricuspid valve of the patient.

As used herein the term "septal leaflet annulus" is intended to mean an annulus on a septal leaflet side of the tricuspid valve including three valve leaflets referred to as the anterior leaflet, the posterior leaflet, and the septal leaflet.

Embodiment 3: Aortic Valve

In the present embodiment, a prosthetic valve forming template and a prosthetic valve used in valve replacement procedure of a human aortic valve will be described. Description about the structure common to Embodiment 1 will be omitted.

The prosthetic valve forming template 5 of the present embodiment is common to that in the Embodiment 1, and includes; as illustrated in FIG. 2, one base line 6; two drooping lines 7 suspending from both ends of the base line 6; two sidelines 8 extending respectively downward and inward in a semi-parabolic manner from lower ends of the two drooping lines 7; two first horizontal lines 9 extending respectively inward and horizontally from lower ends of the two sidelines 8; two first curved lines 10 extending respectively upward in a parabolic manner from inner ends of the two first horizontal lines 9; two second horizontal lines 11 extending respectively inward and horizontally from inner ends of the two first curved lines 10; and one second curved line 12 extending upward in a parabolic manner from inner ends of the two second horizontal lines 11.

Common to Embodiment 1, the prosthetic valve forming template 5 is placed on the pericardium and the pericardium is cut along an outer periphery thereof to obtain a pericardium having substantially the same shape as the prosthetic valve forming template 5.

Subsequently, a wire is inserted into a bag-shaped space formed by folding back the part of the pericardium having substantially the same shape as the prosthetic valve forming template 5 corresponding to the base line of the prosthetic valve forming template 5 downward, and then the part corresponding to the base line is stitched at several points at positions of having been folded back downward so that the wire is not exposed from the bag-shaped space. This stitching is preferably performed at about eight positions between both ends of the portion corresponding to the base line at substantially the same intervals. The length of the wire is preferably substantially the same as the diameter of the perimeter of the aortic annulus. When the wire is a wire material processed into a helical shape or an accordion-folded shape, the length of the wire means the length of the wire material itself.

Subsequently, the portions corresponding to the two drooping lines are aligned and stitched to form the annulus stitching part 2.

Subsequently, parts corresponding to the two first horizontal lines 9 are overlapped to form an aortic wall stitching part, and parts corresponding to the two second horizontal lines 11 are overlapped to form the aortic wall stitching part.

The prosthetic valve having the configuration described above is implanted into the heart by stitching or crimping the annulus stitching part to the aortic annulus and stitching the aortic wall stitching part to the aortic wall.

As used herein the term "crimp" is intended to mean a method of joining the annulus stitching part and the aortic valve by an action of the wire inserted into the bag-shaped space. Through usage of "crimp" as the method of the joining, simplification of the manipulation of surgical operation and shortening the operation time are achieved as compare to stitching.

Embodiment 4: Pulmonary Valve

In the present embodiment, a prosthetic valve forming template and a prosthetic valve used in valve replacement procedure for a human pulmonary valve will be described. Description about the structure common to Embodiment 1 will be omitted.

The prosthetic valve forming template 5 of the present embodiment is common to that in the Embodiment 1, and includes; as illustrated in FIG. 2, one base line 6; two drooping lines 7 suspending from both ends of the base line 6; two sidelines 8 extending respectively downward and inward in a semi-parabolic manner from lower ends of the two drooping lines 7; two first horizontal lines 9 extending respectively inward and horizontally from lower ends of the two sidelines 8; two first curved lines 10 extending respectively upward in a parabolic manner from inner ends of the two first horizontal lines 9; two second horizontal lines 11 extending respectively inward and horizontally from inner ends of the two first curved lines 10; and one second curved line 12 extending upward in a parabolic manner from inner ends of the two second horizontal lines 11.

Common to Embodiment 1, the prosthetic valve forming template 5 is placed on the pericardium and the pericardium is cut along an outer periphery thereof to obtain a pericardium having substantially the same shape as the prosthetic valve forming template 5.

Subsequently, a wire is inserted into a bag-shaped space formed by folding back the part of the pericardium having substantially the same shape as the prosthetic valve forming template 5 corresponding to the base line of the prosthetic valve forming template 5 downward, and then the part corresponding to the base line is stitched at several points at positions of having been folded back downward so that the wire is not exposed from the bag-shaped space. This stitching is preferably performed at about eight positions between both ends of the portion corresponding to the base line at substantially the same intervals. A length of the wire is preferably substantially the same as the diameter of a perimeter of the pulmonary annulus. When the wire is a wire material processed into a helical shape or an accordion-folded shape, the length of the wire means the length of the wire material itself.

Subsequently, the portions corresponding to the two drooping lines are aligned and stitched to form the annulus stitching part 2.

Subsequently, parts corresponding to the two first horizontal lines 9 are overlapped to form a pulmonary artery wall stitching part, and parts corresponding to the two second horizontal lines 11 are overlapped to form the pulmonary artery wall stitching part.

The prosthetic valve having the configuration described above is implanted into the heart by stitching or crimping the annulus stitching part to the aortic annulus and stitching the pulmonary artery wall stitching part to the pulmonary artery wall.

INDUSTRIAL APPLICABILITY

The present invention can be applied to prosthetic valves used for valve replacement procedure for therapy for valvular disease.

REFERENCE SIGNS LIST

1 prosthetic valve
2 annulus stitching part
3 anterior papillary muscle stitching part
4 posterior papillary muscle stitching part
5, 15 prosthetic valve forming template
6, 16 base line
7, 17 drooping line
8, 18 sideline
9, 19 first horizontal line
10, 20 first curved line
11, 21 second horizontal line
12 second curved line
101 mitral valve
102 tricuspid valve
103 annulus part
104 valve leaflet
105 tendinous cord
106 papillary muscles
107 aortic valve
108 pulmonary valve

The invention claimed is:

1. A prosthetic valve forming template for forming a prosthetic valve having an annulus stitching part to be stitched to a mitral annulus, an anterior papillary muscle stitching part to be stitched to an anterior papillary muscle, and a posterior papillary muscle stitching part to be stitched to a posterior papillary muscle, the prosthetic valve forming template comprising:
one base line;
two drooping lines suspending from both ends of the base line;
two sidelines extending respectively downward and inward in a semi-parabolic manner from lower ends of the two drooping lines;
two first horizontal lines extending respectively inward and horizontally from lower ends of the two sidelines;
two first curved lines extending respectively upward in a parabolic manner from inner ends of the two first horizontal lines;
two second horizontal lines extending respectively inward and horizontally from inner ends of the two first curved lines; and
one second curved line extending upward in a parabolic manner from inner ends of the two second horizontal lines.

2. The prosthetic valve forming template according to claim 1, wherein a direct distance ($Y1_M$) from the base line to the first horizontal line and a direct distance ($Y2_M$) from the base line to the second horizontal line have following lengths, respectively,
$Y1$=107.5% to 109.5% of a length ($Y1_M'$) corresponding to a direct distance from an anterior leaflet annulus to a posterior papillary muscle of the mitral valve, and
$Y2$=107.5% to 109.5% of a length ($Y2_M'$) corresponding to a direct distance from an anterior leaflet annulus to an anterior papillary muscle of the mitral valve.

3. The prosthetic valve forming template according to claim 1, wherein a length ($X_M$) of the base line is a length ($X_M'$) corresponding to a perimeter of the mitral annulus.

4. The prosthetic valve forming template according to claim 2, wherein length of the two drooping lines are respectively lengths of 25 to 35% of the $Y1_M$.

5. A prosthetic valve having an annulus stitching part to be stitched to a tricuspid annulus, a medial papillary muscle stitching part to be stitched to a medial papillary muscle, and a posterior papillary muscle stitching part to be stitched to a posterior papillary muscle, the prosthetic valve forming template comprising:
one base line;
two drooping lines suspending from both ends of the base line;
two sidelines extending respectively downward and inward in a semi-parabolic manner from lower ends of the two drooping lines;
two first horizontal lines extending respectively inward and horizontally from lower ends of the two sidelines;
two first curved lines extending respectively upward in a parabolic manner from inner ends of the two first horizontal lines; and
one second horizontal line connecting inner ends of the two first curved lines.

6. The prosthetic valve forming template according to claim 5, wherein a direct distance ($Y1_T$) from the base line to the first horizontal line and a direct distance ($Y2_T$) from the base line to the second horizontal line have following lengths, respectively,
$Y1_T$=109.5% to 112.5% of a length ($Y1_T'$) corresponding to a direct distance between a septal leaflet annulus and a posterior papillary muscle of the tricuspid valve, and
$Y2_T$=109.5% to 112.5% of a length ($Y2_T'$) corresponding to a direct distance between a septal leaflet annulus and a medial papillary muscle of the tricuspid valve.

7. The prosthetic valve forming template according to claim 5, wherein a length (X) of the base line is a length ($X_T'$) corresponding to a perimeter of the tricuspid annulus.

8. The prosthetic valve forming template according to claim 6, wherein a length of the two drooping lines are respectively lengths of 25 to 35% of the $Y1_T$.

9. A prosthetic valve forming template for forming a prosthetic valve having an annulus stitching part to be stitched or crimped to an aortic annulus, and two aortic wall stitching parts to be stitched to an aortic wall, the prosthetic valve forming template comprising:
one base line;
two drooping lines suspending from both ends of the base line;
two sidelines extending respectively downward and inward in a semi-parabolic manner from lower ends of the two drooping lines;
two first horizontal lines extending respectively inward and horizontally from lower ends of the two sidelines;

two first curved lines extending respectively upward in a parabolic manner from inner ends of the two first horizontal lines;
two second horizontal lines extending respectively inward and horizontally from inner ends of the two first curved lines; and
one second curved line extending upward in a parabolic manner from inner ends of the two second horizontal lines.

10. A prosthetic valve forming template for forming a prosthetic valve having an annulus stitching part to be stitched or crimped to a pulmonary annulus, and two pulmonary artery wall stitching parts to be stitched to a pulmonary artery wall, the prosthetic valve forming template comprising:
one base line;
two drooping lines suspending from both ends of the base line;
two sidelines extending respectively downward and inward in a semi-parabolic manner from lower ends of the two drooping lines;
two first horizontal lines extending respectively inward and horizontally from lower ends of the two sidelines;
two first curved lines extending respectively upward in a parabolic manner from inner ends of the two first horizontal lines;
two second horizontal lines extending respectively inward and horizontally from inner ends of the two first curved lines; and
one second curved line extending upward in a parabolic manner from inner ends of the two second horizontal lines.

11. A prosthetic valve having an annulus stitching part to be stitched to a mitral annulus; an anterior papillary muscle stitching part to be stitched to an anterior papillary muscle; and a posterior papillary muscle stitching part to be stitched to a posterior papillary muscle, the prosthetic valve being made by using a membrane member including:
one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines; and one second curved line extending upward in a parabolic manner from inner ends of the two second horizontal lines,
the annulus stitching part being formed by folding back the base line vertically downward with respect to a plane including the anterior papillary muscle stitching part and the posterior papillary muscle stitching part, and then aligning the two drooping lines with each other and stitching together,
the anterior papillary muscle stitching part being formed by overlapping the two second horizontal lines,
the posterior papillary muscle stitching part being formed by overlapping the two first horizontal lines, and
the prosthetic valve comprising:
a barrel cylindrical part opening vertically upward with respect to a plane including the anterior papillary muscle stitching part and the posterior papillary muscle stitching part, and including the annulus stitching part, and
a bifurcated part continuing from the barrel cylindrical part, the bifurcated part including the anterior papillary muscle stitching part at a distal end and the posterior papillary muscle stitching part at an opposite distal end.

12. The prosthetic valve according to claim 11, wherein the bifurcated part has a shape including secondary tendinous cords to be attached to a center part of an anterior leaflet of the mitral valve and a center part of a posterior leaflet of the mitral valve together as a bunch.

13. The prosthetic valve according to claim 11, wherein a direct distance ($Y1_M$) from the base line to the first horizontal line and a direct distance ($Y2_M$) from the base line to the second horizontal line have following lengths, respectively:
$Y1$=107.5% to 109.5% of a length ($Y1_M'$) corresponding to a direct distance from an anterior leaflet annulus to a posterior papillary muscle of the mitral valve, and
$Y2$=107.5% to 109.5% of a length ($Y2_M'$) corresponding to a direct distance from an anterior leaflet annulus to an anterior papillary muscle of the mitral valve.

14. The prosthetic valve according to claim 11, wherein a length ($X_M$) of the base line is a length ($X_M'$) corresponding to a perimeter of the mitral annulus.

15. The prosthetic valve according to claim 13, wherein the length of the two drooping lines are respectively lengths of 25 to 35% of the $Y1_M$.

16. The prosthetic valve according claim 13, wherein a part from an upper end of the annulus stitching part to a lower end of the anterior papillary muscle stitching part has a length corresponding to the $Y2_M'$, and a part from an upper end of the annulus stitching part to a lower end of the posterior papillary muscle stitching part has a length corresponding to the $Y1_M'$.

17. A prosthetic valve having an annulus stitching part to be stitched to a tricuspid annulus; a medial papillary muscle stitching part to be stitched to a medial papillary muscle; and a posterior papillary muscle stitching part to be stitched to a posterior papillary muscle,
the prosthetic valve being made by using a membrane member including:
one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines;
and one second horizontal line connecting inner ends of the two first curved lines,
the annulus stitching part being formed by folding back the base line vertically downward with respect to a plane including the medial papillary muscle stitching part and the posterior papillary muscle stitching part, and then aligning the two drooping lines with each other and stitching together,
the medial papillary muscle stitching part being formed by overlapping the one second horizontal lines,
the posterior papillary muscle stitching part being formed by overlapping the two first horizontal lines, and
the prosthetic valve comprising:
a barrel cylindrical part opening vertically upward with respect to a plane including the medial papillary muscle stitching part and the posterior papillary muscle stitching part, and including the annulus stitching part, and a bifurcated part continuing from the barrel cylindrical part, the bifurcated part including the medial papillary muscle stitching part at a distal end and the posterior papillary muscle stitching part at an opposite distal end.

18. The prosthetic valve according to claim 17, wherein a direct distance ($Y1_T$) from the base line to the first horizontal line and a direct distance ($Y2_T$) from the base line to the second horizontal line have following lengths, respectively:

Y1=109.5% to 112.5% of a length ($Y1_T'$) corresponding to a direct distance from a septal leaflet annulus to a posterior papillary muscle stitching part of the tricuspid leaflet, and Y2=109.5% to 112.5% of a length ($Y2_T'$) corresponding to a direct distance from the septal leaflet annulus to a medial papillary muscle stitching part of the tricuspid leaflet.

19. The prosthetic valve according to claim 17, wherein a length ($X_T$) of the base line is a length ($X_T'$) corresponding to a perimeter of the tricuspid annulus.

20. The prosthetic valve according to claim 18, wherein the length of the two drooping lines are respectively lengths of 25 to 35% of the $Y1_T$.

21. The prosthetic valve according to claim 18, wherein a part from an upper end of the annulus stitching part to a lower end of the medial papillary muscle stitching part has a length corresponding to the $Y2_T'$, and a part from the upper end of the annulus stitching part to a lower end of the posterior papillary muscle stitching part has a length corresponding to the $Y1_T'$.

22. A prosthetic valve having an annulus stitching part to be stitched or crimped to an aortic annulus, and two aortic wall stitching parts to be stitched to an aortic wall, the prosthetic valve being made by using a membrane member including:

one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines; and one second curved line extending upward in a parabolic manner from inner ends of the two second horizontal lines, the annulus stitching part being formed by folding back the base line vertically downward with respect to a plane including the two aortic wall stitching parts, and then aligning the two drooping lines with each other and stitching together, one of the aortic wall stitching parts is formed by overlapping the two second horizontal lines, one of the aortic wall stitching parts is formed by overlapping the two first horizontal lines, the prosthetic valve further comprising:

a barrel cylindrical part opening vertically upward with respect to a plane including the two aortic wall stitching parts, and including the annulus stitching part, and a bifurcated part continuing from the barrel cylindrical part, the bifurcated part including the two aortic wall stitching parts at distal ends thereof.

23. The prosthetic valve according to claim 22, wherein the annulus stitching part is formed by inserting a wire into a bag-shaped space formed by folding back the base line vertically downward.

24. A prosthetic valve having an annulus stitching part to be stitched or crimped to a pulmonary annulus, and two pulmonary artery wall stitching parts to be stitched to a pulmonary artery wall, the prosthetic valve being made by using a membrane member including:

one base line; two drooping lines suspending from both ends of the base line; two sidelines extending respectively downward and inward in a semi-parabolic manner from lower ends of the two drooping lines; two first horizontal lines extending respectively inward and horizontally from lower ends of the two sidelines; two first curved lines extending respectively upward in a parabolic manner from inner ends of the two first horizontal lines; two second horizontal lines extending respectively inward and horizontally from inner ends of the two first curved lines; and one second curved line extending upward in a parabolic manner from inner ends of the two second horizontal lines, the annulus stitching part being formed by folding back the base line vertically downward with respect to a plane including the two pulmonary artery wall stitching parts, and then aligning the two drooping lines with each other and stitching together, one of the pulmonary artery wall stitching parts is formed by overlapping the two second horizontal lines, one of the pulmonary artery wall stitching parts is formed by overlapping the two first horizontal lines, the prosthetic valve comprising:

a barrel cylindrical part opening vertically upward with respect to a plane including the two pulmonary artery wall stitching parts, and including the annulus stitching part, and a bifurcated part continuing from the barrel cylindrical part, the bifurcated part including the two pulmonary artery wall stitching parts at distal ends thereof.

25. The prosthetic valve according to claim 24, wherein the annulus stitching part is formed by inserting a wire into a bag-shaped space formed by folding back the base line vertically downward.

* * * * *

UNITED STATES PATENT AND TRADEMARK OFFICE
CERTIFICATE OF CORRECTION

PATENT NO. : 11,406,494 B2
APPLICATION NO. : 17/267763
DATED : August 9, 2022
INVENTOR(S) : Shinka Miyamoto It is certified that error appears in the above-identified patent and that said Letters Patent is hereby corrected as shown below:

In the Claims

Claim 16, Column 18, Line 27, after "according" insert -- to --.

Signed and Sealed this
Thirty-first Day of January, 2023

Katherine Kelly Vidal
*Director of the United States Patent and Trademark Office*